United States Patent [19]

McRea et al.

[11] Patent Number: 5,324,253

[45] Date of Patent: Jun. 28, 1994

[54] CANNULA APPARATUS AND SYSTEM FOR HEPARIN REMOVAL FROM BLOOD

[76] Inventors: James C. McRea, 6864 S. 300 West, Midvale, Utah 84047; Robert J. Todd, 3420 S. 3610 East, Salt Lake City, Utah 84109

[21] Appl. No.: 844,240

[22] Filed: Mar. 2, 1992

[51] Int. Cl.$^5$ ............................................. A61M 25/00
[52] U.S. Cl. .................................. 604/282; 604/284; 604/280; 604/4
[58] Field of Search .................. 604/4, 5, 6, 52, 53, 604/93, 94, 104, 264, 282, 284, 280

[56] References Cited

U.S. PATENT DOCUMENTS

| | | | |
|---|---|---|---|
| 3,430,631 | 3/1969 | Abramson | 604/282 |
| 3,742,946 | 7/1973 | Grossman | 128/214 R |
| 4,248,704 | 2/1981 | Marconi et al. | 210/632 |
| 4,361,484 | 11/1982 | Larsson et al. | 210/632 |
| 4,362,155 | 12/1982 | Shurkovich | 128/214 R |
| 4,381,775 | 5/1983 | Nosé et al. | 604/6 |
| 4,402,940 | 9/1983 | Nosé et al. | 424/101 |
| 4,405,313 | 9/1983 | Sisley et al. | 604/264 X |
| 4,614,513 | 9/1986 | Besinger | 604/6 |
| 4,623,327 | 11/1986 | Mahurkar | 604/4 |
| 4,639,243 | 1/1987 | Schmidt et al. | 604/6 |
| 4,639,252 | 1/1987 | Kelly et al. | 604/282 |
| 4,643,711 | 2/1987 | Bates | 604/4 |
| 4,696,670 | 9/1987 | Ohnishi et al. | 604/49 |
| 4,800,016 | 1/1989 | Yang | 210/206 |
| 4,804,359 | 2/1989 | Grunwald et al. | 604/284 X |
| 4,863,611 | 9/1989 | Bernstein et al. | 210/661 |
| 4,908,354 | 3/1990 | Seidel et al. | 514/21 |
| 4,980,068 | 12/1990 | Lavender | 210/651 |
| 4,987,085 | 1/1991 | Allen et al. | 436/169 |
| 4,990,132 | 2/1991 | Unger et al. | 604/6 |
| 5,013,296 | 5/1991 | Buckberg et al. | 604/44 |
| 5,021,045 | 6/1991 | Buckberg et al. | 604/53 |
| 5,106,368 | 4/1992 | Uldall et al. | 604/4 X |

*Primary Examiner*—Robert A. Hafer
*Assistant Examiner*—Sam Rimell
*Attorney, Agent, or Firm*—Madson & Metcalf

[57] ABSTRACT

A system for selective removal of certain components from plasma drawn from a patient comprises an extracorporeal blood circulation circuit and a cannula. The extracorporeal blood circulation circuit has an uptake line for transporting blood from the patient, a plasma separator, and a return line connected to the plasma separator for transporting selectively depleted blood from the plasma separator to the patient. The plasma separator is connected to the uptake line for receiving the blood, selectively removing plasma components (e.g., heparin) by separating plasma from whole blood and interfacing such plasma with an adsorption substrate, recombining depleted plasma, and reinfusing selectively depleted blood into the return line for transport to the patient. The cannula has an uptake conduit with an intake end and an exit end, and a return conduit, connected to the uptake conduit, with an outflow end and an entry end. The exit end is connected to the uptake line of the bypass circuit and the entry end is connected to the return line of the bypass circuit. Structure at the outflow end of the return conduit alters the direction of flow and directs selectively depleted blood being returned to the patient into the right atrium of the patient's heart when the intake end of the uptake conduit is disposed within the patient's inferior vena cava. An alternative cannula with washers may be inserted into a venous return cannula whereby recirculation and pooling of the selectively depleted blood is prevented.

12 Claims, 5 Drawing Sheets

CANNULA APPARATUS AND SYSTEM FOR HEPARIN REMOVAL FROM BLOOD

FIELD OF THE INVENTION

The present invention relates to a dual flow cannula used in conjunction with an extracorporeal blood circulation circuit for the removal of certain components from blood, and more particularly to a system comprising a cannula and bypass circuit with a plasma separator through which heparinized blood passes and is deheparinized in order to avoid the administration of protamine.

BACKGROUND OF THE INVENTION

During most cardiopulmonary bypass surgery procedures, the patient is administered heparin for anticoagulation. Subsequent to the cardiopulmonary bypass surgery, it becomes necessary to reverse the anticoagulation state. Typically, protamine sulfate is administered to reverse the heparin-induced anticoagulation. Heretofore, there has been no viable alternative to the administration of protamine for heparin reversal short of allowing the patient to metabolize and eliminate the heparin.

Administering protamine has raised concerns in the medical community because several types of adverse reactions to protamine in the presence of heparin have occurred. Adverse reactions that have been documented include systemic and pulmonary edema, fatal anaphylaxis, thrombocytopenia and altered platelet function, complement activation, and postoperative heparin rebound. It has been estimated that anywhere from 3,500 to over 70,000 open heart patients each year are affected by adverse reactions upon administration of protamine in the United States alone. Despite efforts to circumvent potential problems, patients that become hypertensive because of the administration of protamine are still being encountered. As a consequence, there is some anticipation that more fragile, aging and diabetic patients are at greater risk of adverse effects.

Research seems to indicate that the formation of the insoluble protamine-heparin complex is key to initiating many of the adverse hemodynamic responses. Such responses are not seen in the administration of protamine alone prior to any heparinization. Consequently, there is some pressure to solve the heparin removal problem by avoiding the use of protamine.

Although there are developments that may reduce the need for the administration of heparin as an anticoagulant for extracorporeal procedures, the need for achieving anticoagulation in the surgical field continues. Hence, the need to counteract the anticoagulant effect of heparin will remain.

An additional concern is that any device or method used to reverse the heparin must not compromise the cardiopulmonary bypass circuit or the patient. Avoidance of additional incisions or operative procedures is paramount for the well-being of the patient and would minimize the possibility of complications.

Hence, it would be a significant advance in the art if reversal of heparin could be accomplished using a cannula that can be inserted rapidly into the same incision or even the same venous return cannula used for the cardiopulmonary bypass circuit during the surgery, and can be removed rapidly to permit reintroduction of the cardiopulmonary bypass circuit used during the surgery if the surgeon believes such is necessary. It would be a further advance if a system utilizing the cannula and a plasma separator could be used as a high flow extracorporeal blood circulation circuit to remove selectively certain non-cellular blood components.

OBJECTS AND BRIEF SUMMARY OF THE INVENTION

In view of the foregoing needs and problems experienced by clinicians in reversing the anticoagulation effects of heparin and the adverse reactions to the administration of protamine, it is a primary object of the present invention to provide an access to a system for the removal of heparin from the blood of a bypass patient without administering protamine and without compromising the bypass circuit.

Another object of the present invention is to provide a veno-venous access to a system for the removal of heparin from blood wherein the access has structure which prevents recirculation of the heparin depleted blood through the system.

It is another object of the present invention to provide an apparatus which can safely and effectively reverse the anticoagulation state, subsequent to cardiopulmonary bypass.

A further object of the present invention is to provide a separate extracorporeal blood circulation circuit to be used at the end of cardiopulmonary bypass surgery which exposes heparinized blood to an adsorbing substrate and reinfuses the heparin depleted blood into the patient.

Another object of the present invention is to provide a cannula for use with a separate extracorporeal blood circulation circuit which can be positioned to extract heparinized blood from the patient's inferior vena cava while simultaneously directing heparin depleted blood into the right atrium of the patient's heart.

Still another object of the present invention is to provide a cannula that can be inserted rapidly into the same incision used for the cardiopulmonary bypass circuit during the surgery.

An additional object of the present invention is to provide a cannula that can be removed rapidly to permit reintroduction of the cardiopulmonary bypass circuit used during the surgery if the surgeon believes such is necessary.

It is another object of the present invention to provide an embodiment of the cannula that can be inserted into a dual drainage venous return cannula which has been disconnected from a cardiopulmonary bypass circuit but has not been removed from its disposition within the inferior vena cava, whereby heparinized blood can be extracted from the patient's inferior vena cava while directing heparin depleted blood into the vicinity of the right atrium of the patient's heart.

A further object of the present invention is to provide a system whereby certain blood components may be selectively removed and a selective adsorption depletive blood returned to the patient.

The foregoing objects are accomplished by an apparatus of the present invention which utilizes a dual lumen cannula and a plasma separator in an extracorporeal blood circulation circuit that can be inserted after a cardiopulmonary bypass circuit is used during surgery.

In one preferred embodiment of the present invention a system for selective removal of non-cellular blood components from a cardiopulmonary bypass patient is used which comprises an extracorporeal blood circulation circuit and a cannula. The extracorporeal blood circulation circuit has an uptake line for transporting blood from the patient, a plasma separator, and a return line connected to the plasma separator for transporting the heparin depleted blood from the plasma separator to the patient. The plasma separator is connected to the uptake line for receiving the blood, selectively removing heparin from the blood by interface with an adsorbing substrate within the plasma separator, and reinfusing heparin depleted blood into the return line for transport to the patient.

The plasma separator utilizes a membrane filter and an adsorbing substrate to selectively remove certain non-cellular blood components. The membrane filter is a semipermeable membrane which serves as a separating membrane between the blood phase and the adsorbing substrate. Blood plasma that passes through the membrane filter interfaces with the adsorbing substrate. The adsorbing substrate may contain various sorbent ligands such as immobilized enzymes, proteins, peptides and/or antibodies which may interact with plasma components thereby preventing such plasma components from passing back through the membrane filter to the whole blood phase. In this manner, only selective adsorption depletive blood is reinfused to the patient.

The cannula is designed for disposition within the patient and is connected to an extracorporeal blood circulation circuit. The cannula has an uptake conduit having an intake end and an exit end, and a return conduit (connected to the uptake conduit) which has an outflow end and an entry end. The exit end of the uptake conduit is connected to the uptake line of the extracorporeal blood circulation circuit. The entry end of the return conduit is connected to the return line of the extracorporeal blood circulation circuit. At the outflow end of the return conduit is a structure that alters the direction of flow and directs heparin depleted blood being returned to the patient. The structure is configured to direct the heparin depleted blood into the right atrium of the patient's heart when the intake end of the uptake conduit is disposed within the patient's inferior vena cava. By directing the heparin depleted blood as described, recirculation of the heparin depleted blood through the uptake conduit of the cannula can be avoided.

In another preferred embodiment of the present invention a dual lumen cannula is provided which is designed for insertion into a dual drainage venous return cannula which has been disconnected from a cardiopulmonary bypass circuit but has not been removed from its disposition within the inferior vena cava. With this embodiment, the dual lumen cannula is provided with a pair of washers. One washer, the lower washer, is positioned about the uptake conduit between the intake end and the outflow end of the return conduit. This washer is positioned to prevent recirculation of the heparin depleted blood back through the extracorporeal blood circulation circuit. The other washer, the upper washer, is disposed about both the uptake conduit and the return conduit to prevent unwanted backwash or pooling of blood within the dual drainage venous return cannula. The upper washer and lower washer are positioned such that the outflow end of the return conduit is between the pair of washers. In this manner, when the cannula with washers is inserted into a dual drainage venous return cannula, the washers seal against the interior wall of the dual drainage venous return cannula to form a small chamber for returning heparin depleted blood and from which such blood flows through openings in the venous return cannula into the right atrium of the patient's heart.

The washers of this preferred embodiment may comprise a diaphragm cup washer, a balloon washer, or any other suitable washer capable of sealing the inside of the venous return cannula to prevent recirculation and the pooling of blood within the venous return cannula.

Although the focus of this application is the cannula used to access an extracorporeal blood circulation circuit system for heparin removal and can be used in connection with surgical procedures where blood is heparinized such as cardiopulmonary bypass, hemodialysis, angioplastic procedures, plasmapheresis, autotransfusion and hemoconcentration, the cannula and extracorporeal blood circulation circuit system of the present invention can be used with other selective plasma sorbent systems. Plasma sorbent systems that involve separation, interaction and recombination are particularly suitable. Potential applications of the system include the removal of autoantibodies using sorbents such as immobilized Protein-A; removal of circulating toxins and tumor antigens using sorbents such as immobilized monoclonal antibodies and specific immobilized ligands; removal of protein bound toxins and drugs; selective removal of plasma components using immobilized enzymes as sorbents; and removal of cholesterol (low density lipoproteins, LDL) using sorbents specific to LDL.

These and other objects and features of the present invention will become more fully apparent through the following description and appended claims taken in conjunction with the accompanying drawings.

BRIEF DESCRIPTION OF THE DRAWINGS

In order that the manner in which the above-recited and other advantages and objects of the invention are obtained, a more particular description of the invention briefly described above will be rendered by reference to specific exemplary embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Referring now specifically to the drawings, wherein like numerals indicate like parts throughout, the system of the present invention for removal of heparin comprises an extracorporeal blood circulation circuit generally designated 10 and a cannula generally designated 12. The extracorporeal blood circulation circuit 10, shown in FIG. 4, has an uptake line 14 for transporting blood from a patient (not shown), a plasma separator generally designated 16, and a return line 18 connected to the plasma separator 16 for transporting the heparin depleted blood from the plasma separator 16 to the patient. The plasma separator 16 is connected to the uptake line 14 for receiving the blood, selectively removing heparin, and reinfusing heparin depleted blood into the return line 18 for transport to the patient.

Figures 1, 2, 2A:
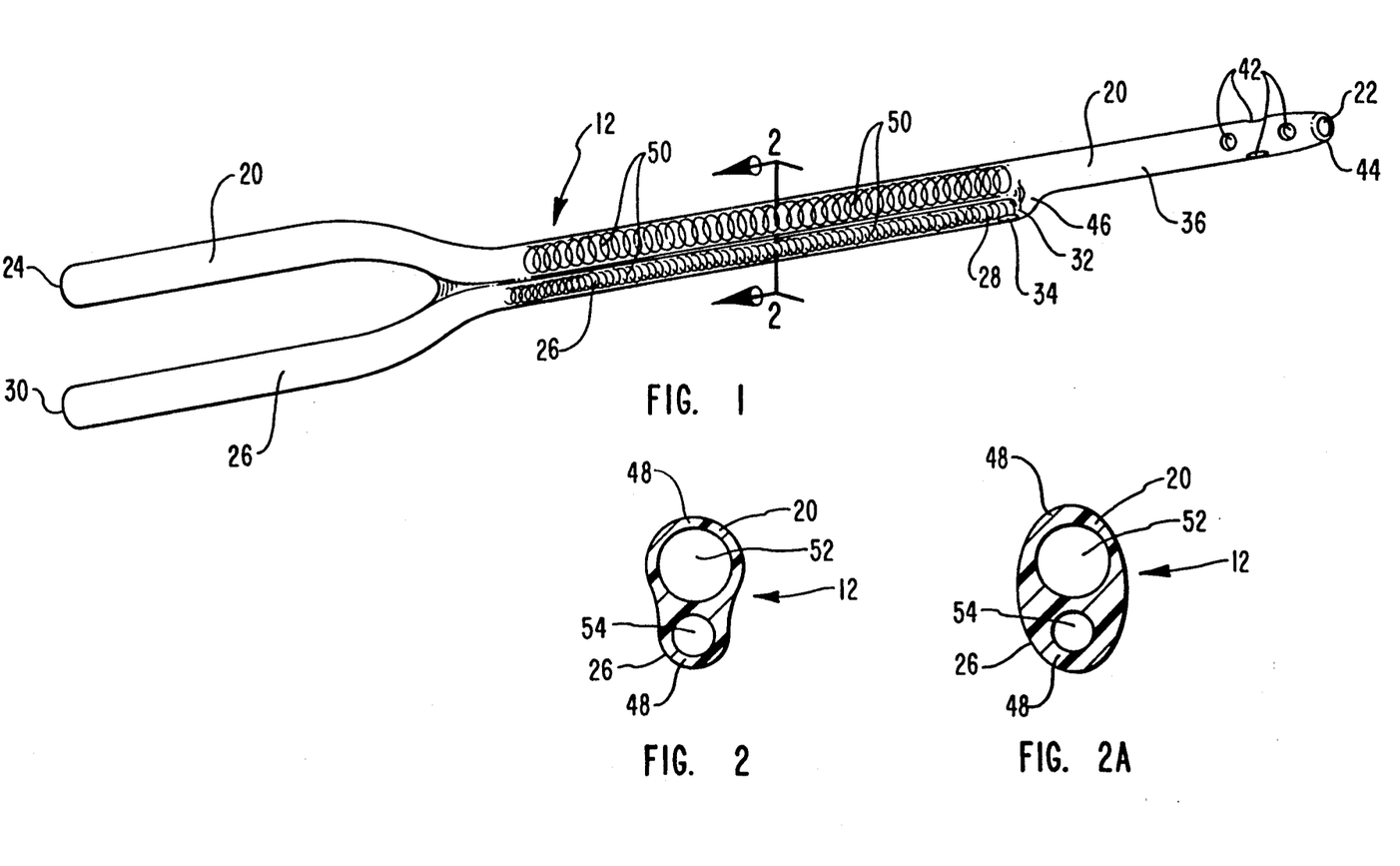
FIG. 1 is a perspective view of a dual lumen cannula of one embodiment of the present invention showing a wire reinforced barrel and one type of dilator portion.
FIG. 2 is a sectional view of the dual lumen cannula of the present invention, without the wire reinforcement, along line 2—2 of FIG. 1.
FIG. 2a is a sectional view of an alternative dual lumen, elliptical barrel cannula.

The cannula 12, shown best in FIG. 1, is designed for disposition within the patient and is capable of connection to the extracorporeal blood circulation circuit 10. The cannula 12 has an uptake conduit 20 having an intake end 22 and an exit end 24, and a return conduit 26, connected in parallel with the uptake conduit 20, which has an outflow end 28 and an entry end 30. The exit end 24 of the uptake conduit 20 is capable of connection to the uptake line 14 of the extracorporeal blood circulation circuit 10 (see FIG. 4). The entry end 30 of the return conduit 26 is capable of connection to the return line 18 of the extracorporeal blood circulation circuit 10 (see FIG. 4). At the outflow end 28 of the return conduit 26 is structure 32 having an exit portal 34 which serves as a directional exit that alters the direction of flow and directs heparin depleted blood being returned to the patient.

Figure 3:
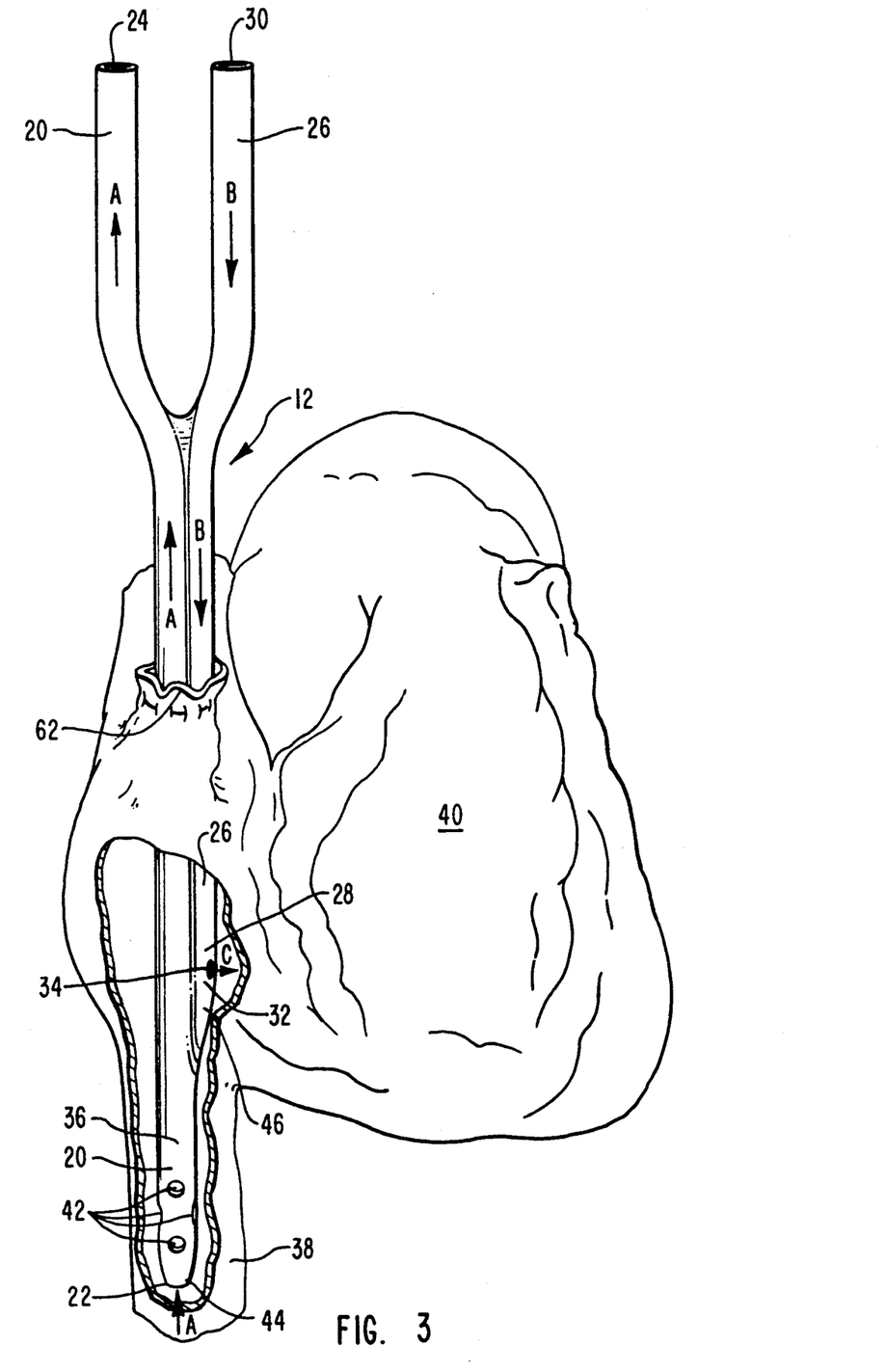
FIG. 3 is a schematic of the dual lumen cannula of the present invention showing the cannula with a dilator as inserted into the venous uptake incision used for cardiopulmonary bypass and illustrating the relative disposition of the uptake lumen in the inferior vena cava and the return lumen in the vicinity of the right atrium of the heart (as shown in cut-away)

As illustrated in FIGS. 1 and 3, the uptake conduit 20 comprises an extension portion 36 which extends beyond the return conduit 26 such that the intake end 22 of the uptake conduit 20 is spaced sufficiently from the outflow end 28 of the return conduit 26 that if the intake end 22 is disposed within a patient's inferior vena cava 38, the outflow end 28 of the return conduit 26 and the exit portal 34 is capable of being positioned in the vicinity of the right atrium of the patient's heart 40. Further, the length of the extension portion 36 is sufficiently long that the intake end 22 is positioned within the flow of blood within the inferior vena cava well upstream of the right atrium so that recirculation of heparin depleted blood is avoided.

In a preferred embodiment of the cannula 12 of the present invention, the extension portion 36 of uptake conduit 20 has a plurality of intake openings 42 and the intake end 22 has a slight taper 44 to facilitate insertion of the cannula 12 into a surgical incision or a venous return cannula and into the patient's venous system. Although the cannula 12 may be constructed without the intake openings 42 and the taper 44, it is preferred to provide a cannula 12 with such features.

To further facilitate the insertion of the cannula 12 into a patient, it is preferred that the cannula 12 further comprise a dilator portion 46 disposed between the intake end 22 and the outflow end 28. The dilator portion 46 may be constructed in various configurations as illustrated by comparing the dilator portions 46 shown in FIGS. 1 and 3. Although it is preferred that the cannula 12 have a dilator portion 46, it should be understood that a dilator portion 46 may not be necessary. For example, it may not be necessary to have a dilator portion 46 for a cannula 12 to be inserted into a venous return cannula. In such instances, the cannula 12 may be constructed without a dilator portion 46 without departing from the spirit of the invention.

In a preferred embodiment of the cannula 12 of the present invention as shown in FIG. 1, the uptake conduit 20 and the return conduit 26 have walls 48 that are wire 50 reinforced. Such reinforcement facilitates the flow of blood through the cannula 12 by reducing the likelihood of kinking and by maintaining the structural integrity of the cannula 12. There are, however, instances when wire 50 reinforcement is not necessary and the cost of the cannula 12 can be reduced by eliminating the wire 50 reinforcement. Certainly, it should be understood that the cannula 12 may be constructed with limited or no wire 50 reinforcement (see FIGS. 3 and 5) without departing from the spirit and intent of the invention.

Turning now to FIGS. 2 and 2a, alternative transverse sections of the cannula 12 of FIG. 1 (without wire 50 reinforcement) are shown. With each of FIGS. 2 and 2a, the wall 48 of uptake conduit 20 defines an uptake lumen 52 and the wall 48 of return conduit 26 defines a return lumen 54. FIG. 2 shows a configuration in which the wall 48 thickness for uptake conduit 20 is substantially equal to the wall 48 thickness for the return conduit 26, and the dimension or diameter of the uptake lumen 52 is larger than the dimension or diameter of the return lumen 54. FIG. 2a shows an alternative configuration in which the wall 48 thickness for uptake conduit 20 is substantially equal to the wall 48 thickness for the return conduit 26. The configuration shown in FIG. 2a also illustrates a wall 48 periphery that is substantially elliptical. Although it is preferred that the wall 48 thicknesses be substantially equal, such need not be the case. Also, it is preferred that the uptake lumen 52 have a larger dimension or diameter that the return lumen 54, but other dimensions or diameters may be used without departing from the spirit of the invention.

As best shown in FIG. 3, the exit portal 34 of structure 32 is configured to direct the heparin depleted blood into the right atrium of the patient's heart 40 when the intake end 22 of the uptake conduit 20 is disposed within the patient's inferior vena cava 36. Structure 32 changes the direction of flow of the heparin depleted blood returning to the patient.

The general direction of the flow of blood (heparinized) being removed through uptake conduit 20 from the patient for selective adsorption/depletion is illustrated by Arrows A in FIG. 3. The general direction of the flow of heparin depleted blood being returned to the patient through return conduit 26 is illustrated by Arrows B. Structure 32 alters the direction of the flow of the heparin depleted blood so that it exits the exit portal 34 generally in the direction of the right atrium of the heart 40 as illustrated by Arrow C in FIG. 3, which direction is generally transverse to the directions illustrated by Arrows A and B and the flow of blood through the inferior vena cava. By altering the flow direction of the heparin depleted blood as it exits the cannula 12, recirculation of the heparin depleted blood is prevented. Although it is preferred that the heparin depleted blood exits the cannula 12 in a direction which is generally transverse to the direction of flow within the uptake conduit 20 and the return conduit 26, it should be understood that other angles of exit may be used and may prove to be particularly useful if the cannula 12 is used in connection with other surgical procedures.

Figure 4:
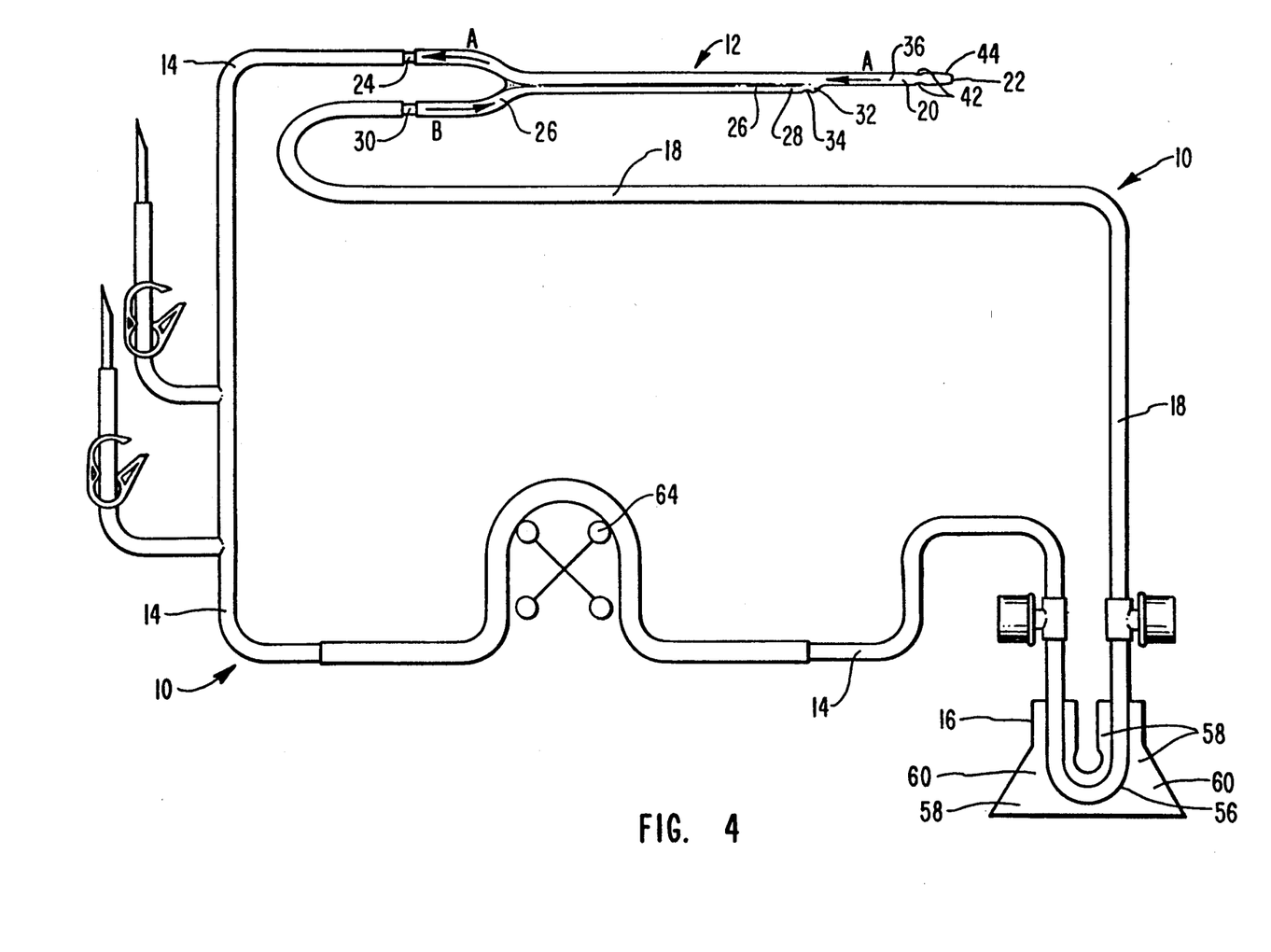
FIG. 4 is a schematic of the extracorporeal blood circulation circuit system of the present invention showing uptake and return lines connected to a plasma separator and the cannula.

With reference now to FIG. 4, the plasma separator 16 utilizes a membrane filter 56 and an adsorption substrate 58 to separate blood plasma from the cellular components of the blood and to interface the blood plasma with the adsorption substrate 58 to selectively remove certain components from the plasma. The membrane filter 56 is semipermeable and serves to separate the cellular components of the blood which cannot permeate the membrane filter 56 from the plasma and plasma components which permeate the membrane filter 56 and interface with the adsorption substrate 58 which is disposed in a plasma chamber 60 within the plasma separator 16. The adsorption substrate 58 may contain various sorbent ligands such as immobilized enzymes, proteins, polypeptides, ionically charged linear polymers, and/or antibodies to which various plasma components such as heparin may adhere by adsorption thereby preventing such plasma components from passing back through the membrane filter 58. The selectively depleted plasma passes back through the membrane filter 58 to recombine with the cellular components of the blood. Hence, the plasma separator 16 is suitable for use as a simultaneous heparin removal and reinfusion system where only heparin depleted blood is reinfused to the patient.

The membrane filter 56 can be a hollow fiber membrane filter made of any blood compatible material having suitable pore size to allow passage of desired solute materials such as plasma and plasma components into the plasma chamber, even those of high molecular weight, and yet retain the blood cells and platelets within the lumen of the hollow fiber membrane filter 56. However, the material from which the membrane filter 56 is constructed must have a pore size that prevents the passage therethrough of heparin as adsorbed by a sorbent in adsorption substrate 58. Hence, heparin will be captured by an adsorption process within the plasma chamber 60.

The adsorption substrate 58 that is disposed within the plasma chamber 60 may comprise various sorbents. For heparin removal, the collection of heparin by a solid substrate by affinity adsorption techniques is documented in the art. One preferred sorbent for heparin removal is poly(L)lysine agarose beads. A more detailed description of the use of sorbents, immobilized enzymes, and antibodies for the removal of various plasma components, can be found in the co-pending and commonly owned application Ser. No. 07/736,405 and entitled, "A Plasma Filter Sorbent System for Removal of Components From Blood; Improved Mass Transport System," and listing Udipi Shettigar and James C. McRea as the inventors.

As an example only and without intending to limit the invention, in the case of cardiopulmonary bypass surgery, the heparinized blood will pass through the extracorporeal blood circulation circuit system which is inserted after the cardiopulmonary bypass is completed in order to remove the heparin and avoid the requirement of administering protamine. As explained above, the cannula 12 is a veno-venous dual lumen single barrel cannula that can be inserted into the venous uptake incision 62 (see FIG. 3) of the cardiopulmonary bypass procedure. The intake end 22 of the uptake conduit 20 of the cannula 12 would insert retrograde into the inferior vena cava 38 and take up heparinized blood from the patient to the plasma separator 16. A roller pump 64 would move blood under positive pressure to the plasma separator 16 where heparin is removed. Heparin depleted blood is then returned to the patient through the return conduit 26 of the dual lumen cannula 12 and is directed towards the right atrial inflow.

Figure 5:
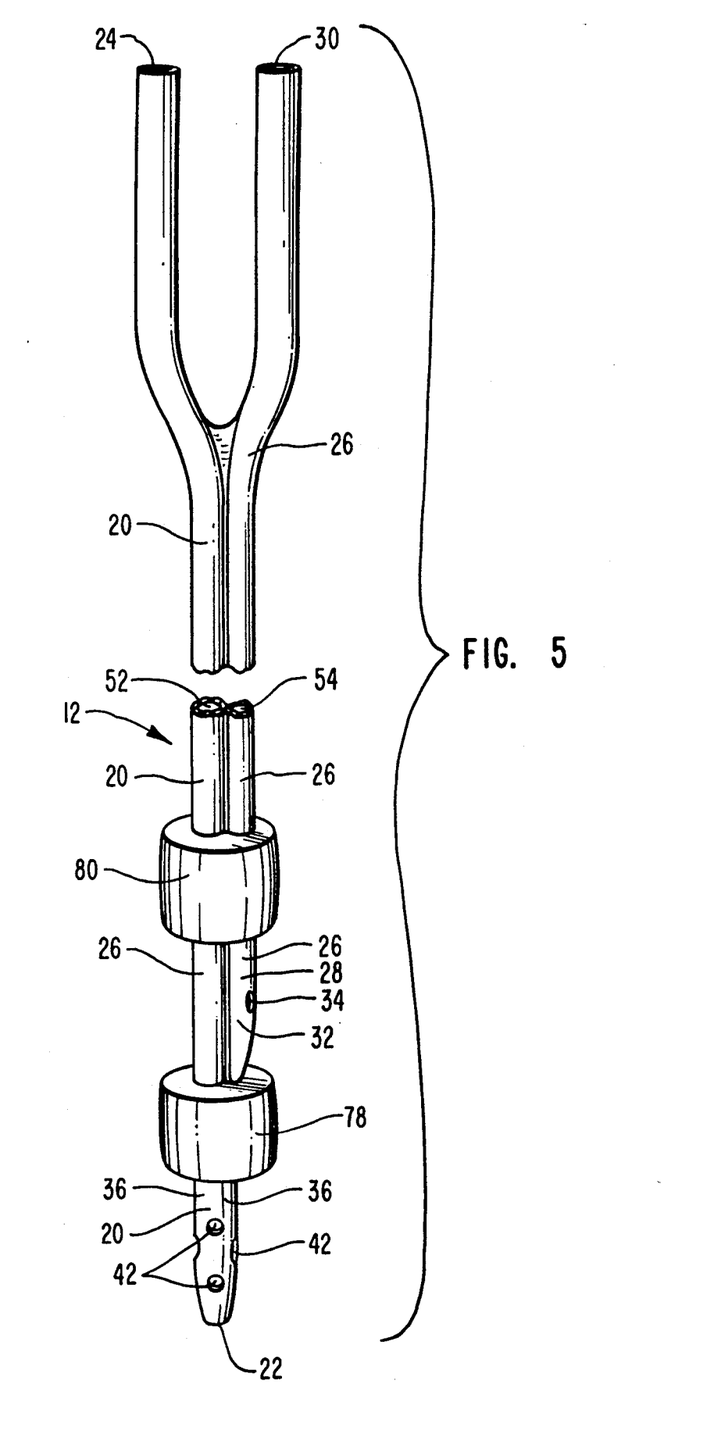
FIG. 5 is a perspective view of an alternative embodiment of the cannula of the present invention showing a pair of washers disposed in spaced relationship about the barrel of the cannula.
Figure 6:
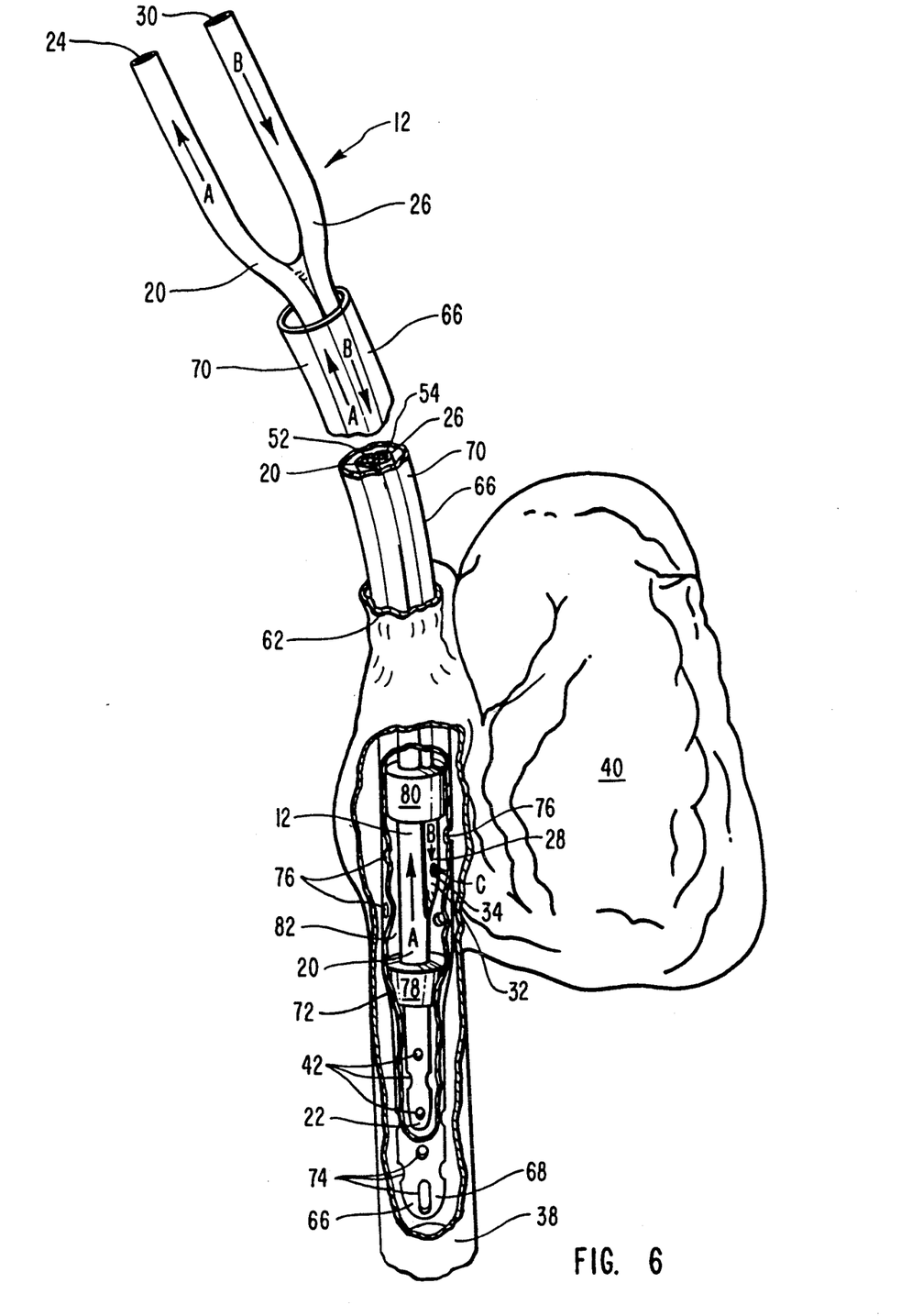
FIG. 6 is a schematic view of the alternative embodiment of the cannula showing its disposition (in cutaway) within a dual drainage venous return cannula.

Turning now to FIGS. 5 and 6, another preferred embodiment of the present invention is illustrated in which a cannula 12 is designed for insertion into a dual drainage venous return cannula 66 which has been disconnected from a cardiopulmonary bypass circuit but has not been removed from its disposition within the inferior vena cava 38. A type of venous return cannula 66 which is particularly suitable is the cannula disclosed in U.S. Pat. No. 4,639,252, entitled "Venous Return Catheter," issued Jan. 27, 1987 to Michael N. Kelly, John B. Foster, and Robert D. Foster. This type of venous return cannula 66 has a distal portion 68, a proximal portion 70, and a transition portion 72. In the distal portion 68 are openings 74 for receiving blood flow from the inferior vena cava 38. In the proximal portion 70 are drainage openings 76.

The cannula 12 is provided with a pair of washers, the lower washer 78 is positioned about the uptake conduit 20 between the intake end 22 and the outflow end 28 of the return conduit 26, and the upper washer 80 is disposed about both the uptake conduit 20 and the return conduit 26. When the cannula 12 is inserted into the venous return cannula 66, the lower washer 78 seats in sealing engagement with the interior wall of the transition portion 72 to prevent recirculation of the heparin depleted blood back through the extracorporeal blood circulation circuit 10. The upper washer 80 is positioned in sealing engagement with the interior wall of the proximal portion 70 to prevent unwanted backwash or pooling of blood within the dual drainage venous return cannula 66. The lower washer 78 and upper washer 80 are spaced from each other and positioned such that the outflow end 28 of the return conduit 26 is between the pair of washers 78, 80. In this manner, the washers 78, 80 together with the interior wall of the venous return cannula 66 form a small chamber 82 for receiving heparin depleted blood and from which such blood flows through the drainage openings 76 in the venous return cannula 66 into the right atrium of the patient's heart 40. Importantly, the small chamber 82 must be sufficiently small so that the heparin depleted blood will not pool within the small chamber 82 because pooling heparin depleted blood will coagulate and could occlude the drainage openings 76.

The washers 78, 80 of this preferred embodiment may comprise any of a number of types of washers such as a diaphragm cup washer, a balloon washer, or any other suitable washer capable of sealing the inside of the venous return cannula 66 to prevent recirculation and the pooling of blood within the venous return cannula 66.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A cannula for disposition within a venous return cannula disposed within the inferior vena cava of a patient and connection with an extracorporeal blood circulation circuit to remove blood from the patient's venous system, remove selectively certain components within the blood, and return the selectively depleted blood to the right atrium of the patient's heart, comprising:

an uptake conduit for transporting blood from the patient to the extracorporeal blood circulation circuit, said uptake conduit comprising an intake end capable of disposition within the inferior vena cava and an exit end capable of connection to the extracorporeal blood circulation circuit;

a return conduit connected to said uptake conduit for transporting selectively depleted blood from the extracorporeal blood circulation circuit to the patient, said return conduit comprising an outflow end and an entry end, said entry end being capable of connection to the extracorporeal blood circulation circuit;

a pair of washers for seating in sealing engagement with the venous return cannula, comprising:

a lower washer disposed about said uptake conduit between said intake end and said outflow end of said return conduit; and an upper washer disposed about said uptake conduit and said return conduit and spaced from said lower washer such that said outflow end is positioned between said pair of washers; and means for directing selectively depleted blood into a chamber formed by said pair of washers and the venous return cannula and then from said chamber to the right atrium of the patient's heart, said means for directing selectively depleted blood being connected to said outflow end of said return conduit.

2. A cannula as set forth in claim 1, wherein said uptake conduit extends beyond said return conduit such that said intake end of said uptake conduit is spaced sufficiently from said outflow end of said return conduit that if said intake end is disposed within the patient's inferior vena cava, said outflow end of said return conduit is capable of being positioned such that said means for directing selectively depleted blood is located in the vicinity of the right atrium of the patient's heart.

3. A cannula as set forth in claim 1, wherein said uptake conduit further comprises a plurality of intake openings disposed adjacent said intake end of said uptake conduit.

4. A cannula as set forth in claim 1, wherein said means for directing selectively depleted blood comprises an exit portal oriented such that selectively depleted blood passing through said return conduit and exit portal exits said exit portal into said chamber in a direction generally transverse to the direction blood passes through said uptake conduit.

5. A cannula as set forth in claim 1, wherein said uptake conduit is wire reinforced.

6. A cannula as set forth in claim 1, wherein said return conduit is wire reinforced.

7. A cannula as set forth in claim 1, wherein said uptake conduit comprises an uptake conduit wall which defines an uptake lumen and said return conduit comprises a return conduit wall which defines a return lumen.

8. A cannula as set forth in claim 7, wherein intermediate of said outflow end and said entry end of said return conduit said uptake lumen is disposed substantially parallel to said return lumen.

9. A cannula as set forth in claim 7, wherein the transverse dimension of said uptake lumen is larger than the transverse dimension of said return lumen.

10. A cannula as set forth in claim 7, wherein said uptake conduit wall has substantially the same thickness as said return conduit wall.

11. A cannula as set forth in claim 1, further comprising a wall which circumscribes said uptake conduit and said return conduit.

12. A cannula as set forth in claim 11, wherein the periphery of a transverse section of said wall is generally elliptical.

* * * * *